United States Patent
Prencipe et al.

(10) Patent No.: US 9,566,230 B2
(45) Date of Patent: *Feb. 14, 2017

(54) HYDROPHOBIC TOOTH WHITENING SYSTEM AND METHODS OF USE

(71) Applicant: COLGATE-PALMOLIVE COMPANY, New York, NY (US)

(72) Inventors: Michael Prencipe, Princeton Junction, NJ (US); Suman K. Chopra, Monroe, NJ (US); Michael Collins, Hazlet, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/338,319

(22) Filed: Jul. 22, 2014

(65) Prior Publication Data

US 2014/0335028 A1 Nov. 13, 2014

Related U.S. Application Data

(60) Division of application No. 10/915,125, filed on Aug. 10, 2004, now Pat. No. 8,815,215, which is a continuation-in-part of application No. 10/745,065, filed on Jan. 7, 2004, now abandoned, which is a continuation-in-part of application No. 10/642,458, filed on Aug. 15, 2003, now abandoned.

(51) Int. Cl.

| A61Q 11/00 | (2006.01) |
|---|---|
| A61K 8/22 | (2006.01) |
| A61K 8/89 | (2006.01) |
| A61K 8/25 | (2006.01) |
| A61K 6/00 | (2006.01) |
| A61C 19/06 | (2006.01) |
| A61K 8/81 | (2006.01) |
| A61K 8/891 | (2006.01) |
| A61K 8/895 | (2006.01) |

(52) U.S. Cl.
CPC ............ *A61K 8/89* (2013.01); *A61C 19/066* (2013.01); *A61K 8/22* (2013.01); *A61K 8/8176* (2013.01); *A61K 8/891* (2013.01); *A61K 8/895* (2013.01); *A61Q 11/00* (2013.01)

(58) Field of Classification Search
USPC .......... 424/49, 53, 401; 433/215, 216, 217.1
See application file for complete search history.

(56) References Cited

U.S. PATENT DOCUMENTS

| 3,215,599 A | 11/1965 | Thau et al. |
|---|---|---|
| 3,339,547 A | 9/1967 | Drabkowski |
| 3,376,110 A | 4/1968 | Shiraeff |
| 3,379,193 A | 4/1968 | Monaghan |
| 3,480,557 A | 11/1969 | Shiraeff |
| 3,688,406 A | 9/1972 | Porter et al. |
| 4,514,528 A | 4/1985 | Dhabhar et al. |
| 4,569,955 A | 2/1986 | Dhabhar |
| 4,582,701 A | 4/1986 | Piechota et al. |
| 4,585,836 A | 4/1986 | Homan et al. |
| 4,713,243 A | 12/1987 | Shiraldi et al. |
| 4,948,580 A | 8/1990 | Browning |
| 4,971,782 A | 11/1990 | Rudy et al. |
| 5,059,189 A | 10/1991 | Cilento et al. |
| 5,122,370 A | 6/1992 | Merianos et al. |
| 5,232,702 A | 8/1993 | Pfister et al. |
| 5,310,563 A | 5/1994 | Curtis et al. |
| 5,656,286 A | 8/1997 | Miranda et al. |
| 5,676,932 A | 10/1997 | Wason et al. |
| 5,707,611 A | 1/1998 | Ikemura et al. |
| 5,846,058 A | 12/1998 | Fischer |
| 6,089,869 A | 7/2000 | Schwartz |
| 6,126,443 A | 10/2000 | Burgio |
| 6,306,370 B1 | 10/2001 | Jensen et al. |
| 6,364,665 B1 | 4/2002 | Trettenero |
| 6,419,906 B1 | 7/2002 | Xu et al. |
| 6,514,484 B2 | 2/2003 | Rajaiah et al. |
| 6,565,969 B1 | 5/2003 | Lamon et al. |
| 6,740,311 B2 | 5/2004 | White, Jr. et al. |
| 6,860,736 B2 | 3/2005 | Allred et al. |
| 2001/0021374 A1 | 9/2001 | Montgomery |
| 2002/0137728 A1 | 9/2002 | Montgomery |
| 2002/0141950 A1 | 10/2002 | Chen |
| 2002/0187108 A1 | 12/2002 | Rajaiah et al. |
| 2003/0129148 A1 | 7/2003 | Chen |
| 2003/0194382 A1 | 10/2003 | Chang et al. |
| 2004/0219190 A1 | 11/2004 | Kosti |
| 2005/0036956 A1 | 2/2005 | Fei et al. |
| 2005/0038181 A1 | 2/2005 | Chopra et al. |
| 2007/0122357 A1 | 5/2007 | Glandorf |

FOREIGN PATENT DOCUMENTS

| EP | 0325267 | 5/1994 |
|---|---|---|
| WO | WO 99/62472 | 12/1999 |
| WO | WO 01/01939 | 1/2001 |
| WO | WO 01/01942 | 1/2001 |
| WO | WO 01/01958 | 1/2001 |
| WO | WO 01/85116 | 1/2001 |
| WO | WO 01/76549 | 10/2001 |
| WO | WO 02/34221 | 5/2002 |
| WO | WO 02/43657 | 6/2002 |
| WO | WO 02/074274 | 9/2002 |
| WO | WO 03/094877 | 11/2003 |

*Primary Examiner* — Lezah Roberts

(57) ABSTRACT

A tooth whitening system comprising a dental tray having a surface operable to confront a tooth surface, and a tooth whitening composition comprising a whitening agent and a hydrophobic polymer carrier. The tooth whitening composition is preferably substantially non-water soluble. A tooth whitening kit is also provided using a dental tray and the tooth whitening composition comprising a whitening composition and a hydrophobic polymer carrier.

8 Claims, No Drawings

HYDROPHOBIC TOOTH WHITENING SYSTEM AND METHODS OF USE

CROSS-REFERENCE TO RELATED APPLICATIONS

This application is a divisional of U.S. application Ser. No. 10/915,125 filed on Aug. 10, 2004, which is a continuation-in-part of U.S. patent application Ser. No. 10/754,065 filed on Jan. 7, 2004, which is a continuation-in-part of U.S. patent application Ser. No. 10/642,458 filed on Aug. 15, 2003.

The disclosures of the above applications are incorporated herein by reference.

INTRODUCTION

The present invention relates to tooth whitening systems employing compositions comprising hydrophobic polymers. Embodiments of the present invention include tooth whitening systems having dental trays and employing whitening compositions comprising a hydrophobic polymer carrier and a whitening agent.

There is a general desire for people to have white teeth. Such white teeth are an indication of a good health and in particular good oral care health. A problem is that various foods and the use of tobacco will discolor teeth. Beverages such as coffee, tea and cola beverages can discolor teeth.

As a result various products and procedures have been developed to whiten teeth. These products and procedures are either purchased and/or used directly by the consumer or are applied by a dentist or other professional. The more effective products and procedures are those that are performed by a dental professional.

Typically this consists of the dental professional forming a dental tray from an impression of a person's teeth. Custom dental trays can be created by any of the procedures, well known in the art. After the dental tray is formed to the structure of the teeth a whitening formulation is placed in the tray and the tray placed into the mouth and against the teeth to be treated. A dental tray having whitening composition for in-home use is typically left in the mouth for from about 10 minutes to several hours; i.e., up to 12 or more hours. If the treatment occurs in the dental office, the time of the treatment typically will be from about 0.5 hour to about 2 hours.

The products used solely by consumers primarily comprise whitening strips and brush-on products. Whitening strips are plastic strips with the whitening formulation on one surface. The surface with the whitening formulation is pressed against one's teeth and left in contact with the teeth for about 30 minutes. The plastic strip then is removed. The brush-on products are painted into teeth and the user keeps his/her mouth at least partially open for up to about a minute until the formulation dries onto the teeth. In both cases saliva will dilute and flush the tooth whitening composition from the user's teeth. This occurs more so with strips, since foreign materials (such as, a plastic strip), will enhance saliva flow in the mouth. These products are useful to remove some tooth staining. However, they are typically not as concentrated, and thus not as effective tooth whitening systems, as are dental trays, and in particular the use of dental trays by dental professionals.

A problem with the various whitening compositions that are used in dental trays is that they are substantially soluble in water and saliva. This results in a dilution of the whitening formulation during use. In order to overcome this problem producers of these whitening formulations have increased the concentration of the whitening actives. However, this causes a problem of increased tooth sensitivity, gum irritation and the potential long term for lesions. Another solution disclosed in U.S. Pat. No. 5,846,058 has been to use higher viscosity tooth whitening compositions. This increases dilution time and flush time but is not a full solution to the problem. A better solution to this problem is to use a carrier and actives that are substantially insoluble in water and saliva, the carrier being about fully insoluble in water and saliva. The active must have some solubility in order to attack and remove tooth stains. However, it is preferred that the solubility of the active is relatively low. In this way, tooth whitening compositions with a lower concentration of active can be used to enhance whitening through a longer contact time at a more sustained active concentration.

SUMMARY

The present invention provides tooth whitening systems. Embodiments include a tooth whitening system comprising a dental tray having a surface operable to confront a tooth surface and a tooth whitening composition comprising a whitening agent and a hydrophobic polymer carrier.

In another embodiment, the present invention further provides a method of whitening a surface of a tooth, comprising contacting the surface with a whitening composition contained in a dental tray. The whitening composition comprises a whitening agent and a hydrophobic polymer carrier.

Another embodiment includes a tooth whitening kit, for whitening the surface of a tooth in the oral cavity of a human or other animal subject, comprising (a) a dental tray operable for insertion into the oral cavity of the subject, comprising a reservoir. The kit also comprises (b) a tooth whitening composition comprising a peroxide whitening agent and a hydrophobic siloxane polymer carrier having a viscosity of at least about 50,000 centipoise (cP).

It has been discovered that compositions and methods of this invention afford advantages over whitening compositions among those known in the art including one or more of: enhanced whitening efficacy, providing a higher available concentration of whitening agent, adherence of the whitening composition to the tooth surface even in the presence of saliva and sustained and controlled delivery of the whitening agent for a longer duration of time Further uses, benefits and embodiments of the present invention are apparent from the description set forth herein.

DESCRIPTION

The following definitions and non-limiting guidelines must be considered in reviewing the description of this invention set forth herein. The headings (such as "Introduction" and "Summary,") and sub-headings (such as "Whitening Compositions" and "Methods", for example) used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As referred to herein, all compositional percentages are by weight of the total composition, unless otherwise specified.

Tooth Whitening System

In various embodiments, the present invention provides an improved tooth whitening system that comprises a dental tray and a tooth whitening composition. The tooth whitening composition comprises a whitening agent and a hydrophobic polymer carrier. In various embodiments of the present invention, the whitening composition is a viscous suspension which maintains its consistency during storage. The hydrophobic polymer carrier of the whitening composition is preferably not soluble in water and is stable for longer durations during exposure to saliva and other aqueous solutions found in an oral cavity, as compared to prior art water-soluble whitening solutions.

Whitening Compositions

The present invention provides a whitening composition for use in a tooth whitening system. In one embodiment, the whitening composition comprises a whitening agent and a hydrophobic polymer carrier. The whitening composition may further comprise an adhesion enhancing agent. Other additional ingredients that may be added include those known to one of skill in the art, including one or more of the following components: surfactants, flavoring agents, sweeteners, desensitizing agents, antimicrobial agents, anti-caries agents, anti-calculus agents, anti-inflammatory agents, vitamins, pigments and coloring agents, and enzymes, as will be discussed in greater detail below.

Active ingredients useful herein are optionally present in the compositions of the present invention in safe and effective amounts. A "safe and effective" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

Whitening Agents

In various embodiments, the compositions of the present invention comprise a whitening agent as the main active ingredient. As further discussed below, a "whitening agent" is a material which effects whitening of a tooth surface to which it is applied. In various embodiments, the whitening compositions of this invention comprise a whitening agent selected from the group consisting of peroxides, chlorites, and hypochlorites. Examples of suitable chlorites and hypochlorites include those having alkali or alkaline metal cations and include calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

In one embodiment, the whitening agent comprises a peroxide compound. As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

Peroxide releasing compounds particularly useful in the whitening compositions of the present invention include peroxide containing compounds such as urea peroxide, sodium percarbonate, sodium perborate and polyvinylpyrrolidone-$H_2O_2$ complexes (hereinafter "PVP-$H_2O_2$"). Polyvinylpyrrolidone is also known as poly-N-vinyl-poly-2-pyrrolidone and commonly abbreviated to "PVP". PVP generally refers to a polymer containing vinylpyrrolidone (also referred to as N-vinylpyrrolidone, N-vinyl-2-pyrrolidone and N-vinyl-2-pyrrolidinone) as a monomeric unit. The monomeric unit consists of a polar imide group, four non-polar methylene groups and a non-polar methane group.

Both linear and cross-linked complexes of PVP-$H_2O_2$ are known in the art and are disclosed in U.S. Pat. No. 3,376,110 and U.S. Pat. No. 3,480,557, which are herein incorporated by reference, and have been used in compositions for treating acne vulgaris (U.S. Pat. No. 5,122,370). PVP-$H_2O_2$ complexes are also disclosed in U.S. Pat. No. 5,122,370. PVP-$H_2O_2$ is stable in an anhydrous environment. Upon exposure to highly aqueous environments, such as in the oral cavity, the PVP-$H_2O_2$ dissociates into individual species (PVP polymer and $H_2O_2$). In one embodiment, the PVP-$H_2O_2$ complex is about 80% by weight polyvinylpyrrolidone and 20% by weight $H_2O_2$.

In alternate embodiments, the whitening agent comprises a liquid peroxide solution. The hydrophobic polymer carrier of the whitening composition provides sufficient stability to permit the use of a liquid hydrogen peroxide. The liquid hydrogen peroxide comprises $H_2O_2$ generally contained in an aqueous water-based solution. In some embodiments, the liquid hydrogen peroxide has a concentration of peroxide to the total solution of about 0.5 to about 10%, more preferably 0.5 to 5% by weight). Additionally, a stabilizer may be present. For example, a 3% hydrogen peroxide solution with about 0.1 to about 0.5% of a stabilizer may be used. Acetanilide or a similar organic material can also be used with a pyrophosphate stabilizer such as sodium acid pyrophosphate (about 0.1 to about 1.0%) with a preferred amount of about 0.5%.

In certain embodiments, an agent to enhance release of the peroxide in the oral cavity is present as a part of the peroxide component whitening agent. Polypore® which is an allyl methacrylate crosspolymer available from Amcol health & Beauty Solutions, Inc. is such an enhancing agent.

In various embodiments, the whitening agent of the whitening composition comprises from about 0.1% to about 50%, optionally from about 1% to about 40%, and optionally from about 10% to about 30% of the oral care composition.

Hydrophobic Polymer Carrier

The present invention preferably comprises a carrier that comprises a hydrophobic polymer. The term "hydrophobic" or "water-insoluble" as applied to polymers and as employed herein refers to an organic polymer which is substantially non-aqueous having a water solubility of less than one gram per 100 grams of water at 25° C. Any such polymers that are compatible with the whitening agents previously described above, and which can produce a tooth whitening composition having a viscosity of greater than about 1,000 centipoise (cP) and less than about 900,000 cP, preferably greater than about 10,000 cP and less than about 100,000 cP, more preferably greater than 50,000 cP and less than 900,000 cP, and most preferably from between about 200,000 cP to about 600,000 cP, are preferred in various embodiments of the present invention.

One preferred class of hydrophobic polymers comprise siloxane polymers, which are also generally known in the art as "silicone" polymers. In certain embodiments of the present invention, the hydrophobic polymers in the carrier are those in which a whitening agent can be dispersed and are well known in the art. Many such silicone polymers are commercially available. In various embodiments, a preferred silicone-based hydrophobic polymer is a polyorganosiloxane. One such polyorganosiloxane is produced by condensing a silicone resin and an organosiloxane such as a polydiorganosiloxane. Such hydrophobic polymers are an elastomeric, tacky material, adhesion of which to dental enamel surfaces can be varied by altering the ratio of silicone resin to polydiorganosiloxane in the copolymer molecule. Preferably, the polymers are pressure sensitive hydrophobic polymers specifically designed for pharmaceutical use and are permeable to many drug compounds and find application for the transdermal application of various compounds. In one such embodiment, the silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. A catalyst, for example, an alkaline material, such as ammonia, ammonium hydroxide or ammonium carbonate, can be mixed with the silanol-terminated polydiorganosiloxane and the silicone resin to promote this crosslinking reaction. By copolymerizing the silicone resin with the silanol terminated polydiorganosiloxane, there results a polymer with self adhering properties and the cohesive properties of a soft elastomer matrix characteristic of pressure sensitive polymers being distinguished from the hard, non-elastomeric properties of other silicone resins. In one embodiment, hydrophobic polymers used in the carrier are available from the Dow-Corning Company under the brand name BIO-PSA.

The modification of a ratio of silicone resin to polydiorganosiloxane modifies the tackiness of the hydrophilic polymer. This ratio can be in the range of about 70:30 to about 50:50. For example, the BIO PSA silicone sold by Dow-Corning is available in three silicone resin to silicone polymer ratios namely, 65/35 (low tack), 60/40 (medium tack), 55/45 (high tack). Such a polyorganosiloxane pressure sensitive adhesive is available dissolved in either ethyl acetate solvent or dimethicone.

In various embodiments, the hydrophobic polymer carrier is present in the liquid whitening compositions of the present invention at a concentration of about 1 to about 80% by weight and preferably about 15 to about 40% by weight.

Adhesion Enhancing Agents

In one embodiment of the present invention, the whitening composition further comprises an adhesion enhancing agent, that augments adhesion of the anhydrous whitening composition to the surface of the tooth, i.e., adhesion to the enamel. Adhesion enhancing agents useful with the present invention include inorganic materials as well as organic natural and synthetic polymers. Inorganic materials include amorphous silica compounds which function as thickening agents, and include colloidal silica compounds available under trademarks such as Cab-o-sil fumed silica manufactured by Cabot Corporation and distributed by Lenape Chemical, bound Brook, N.J.; Zeodent 165 from J.M. Huber Chemicals Division, Havre de Grace, Md. 21078; and Sylox 15 also known as Sylodent 15, available from Davison Chemical Division of W.R. Grace Corporation, Baltimore, Md. 21203. In certain embodiments, the inorganic adhesion enhancing material, such as silica, is surface treated to compatibilize the adhesion enhancing agent with the hydrophobic components in the whitening system.

Organic materials which may be included in the compositions of the present invention to enhance the properties of the hydrophobic polymers of the present invention include adhesion enhancing agents such as waxes, inclusive of bees' wax, mineral oil, plastigel, (a blend of mineral oil and polyethylene), petrolatum, white petrolatum, shellac, versagel (blend of liquid paraffin, butene/ethylene/styrene hydrogenated copolymer) polyethylene waxes, microcrystalline waxes, polyisobutene, polyvinyl pyrrolidone/vinyl acetate copolymers, and insoluble polyacrylate copolymers.

Also effective as adhesion enhancing agents are liquid hydrophilic polymers including polyethylene glycols, nonionic polymers of ethylene oxide having the general formula:

wherein n represents the average number of oxyethylene groups. Polyethylene glycols available from Dow Chemical are designated by a number such as 200, 300, 400, 600, 2000 which represents the approximate average molecular weight of the polymer, as well as nonionic block copolymer of ethylene oxide and propylene oxide of the formula:

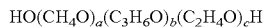

The block copolymer is preferably chosen (with respect to a, b and c) such that the ethylene oxide constituent comprises from about 65 to about 75% by weight, of the copolymer molecule and the copolymer has an average molecular weight of from about 2,000 to about 15,000 with the copolymer being present in the liquid tooth whitening composition in such concentration that the composition is liquid at room temperatures (23° C.).

A particularly desirable block copolymer for use in the practice of the present invention is available commercially from BASF and designated Pluraflo L1220 which has an average molecular weight of about 9,800. The hydrophilic poly(ethylene oxide) block averages about 65% by weight of the polymer.

Adhesion enhancing agents employed in compositions of various embodiments of the invention are present in an amount of from about 0 to about 20% by weight. Preferably, the adhesion enhancing agents are present in an amount of from about 2 to about 15% by weight.

Additional Ingredients

As previously described, many other components may further be included in the whitening compositions of the present invention, and include flavors, sweetening agents, surfactants, anti-microbial agents, anti-inflammatory agents, plaque buffers, vitamins, anti-caries agents, anti-plaque agents, desensitizing agents, coloring agents, pigments and opacifying agents, for example.

In certain embodiments, nonionic surfactants are present in the whitening composition. These surfactants are preferably compatible with the whitening agents and serve as solubilizing, dispersing, emulsifying and wetting agents. In one aspect, surfactants are especially effective to solubilize a flavoring agent, if flavor is desired for the liquid whitening composition. A particularly useful nonionic surfactant is a water soluble polyoxyethylene monoester of sorbitol with a C10 to C18 fatty acid, marketed commercial under the Tween trademark. The Tween surfactants are mixtures of C10 TO C18 fatty acid esters of sorbitol (and sorbitol anhydrides), consisting predominately of the monoester, condensed with about 10-30, preferably about 20, moles of ethyleneoxide. The fatty acid (aliphatic hydrocarbonyl monocarboxylic acid) may be saturated or unsaturated, e.g., lauric, palmitic, stearic, oleic acids. Polysorbate 20 (e.g., Tween 20) is especially preferred and is commonly referred to as polyoxyethylene (20) sorbitan monolaurate. The nonionic surfactant constitutes about 0 to 50% by weight and preferably 0.5 to 40% by weight of the liquid composition.

In an embodiment where the whitening composition has a flavoring agent, the flavoring agent is selected from essential oils, as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is preferably incorporated in the whitening composition of the present embodiment at a concentration of about 0 to about 2% by weight and more preferably about 0.1 to about 0.5% by weight.

In embodiments where the whitening composition is sweetened, a sweetening material is used as an alternative or complement to the flavoring agent. Suitable sweetening agents are water-soluble and include sodium saccharin, sodium cyclamate, xylitol, perillartien, D-tryptophan, aspartame, dihydrochalcones and the like, in concentrations of about 0.01 to about 1% by weight. Sodium saccharin is preferred.

Other ingredients which are included in various embodiments of the liquid whitening composition comprise materials commonly used in the oral care formulations. These include: antimicrobial agents, e.g., Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine and halogenated bisphenolic compounds, such as 2,2' methylenebis-(4-chloro-6-bromophenol); antiinflammatory agents such as ibuprofen, flurbiprofen, aspirin, indomethacine; anticaries agents such as sodium-, calcium-, magnesium- and stannous fluoride, aminefluorides, disodium monofluorophosphate and sodium trimetaphosphate; plaque buffers such as urea, calcium lactate, calcium glycerophosphate and strontium polyacrylates; vitamins such as Vitamin C; plant extracts; desensitizing agents, e.g., potassium citrate, potassium chloride, potassium tartrate, potassium bicarbonate, potassium oxalate, potassium nitrate and strontium salts; agents effective against dental calculus such as pyrophosphate salts including the mono, di, tri and tetra alkali metal and ammonium pyrophosphate and tripolyphosphate salts; biomolecules, e.g., bacteriocins, antibodies, enzymes such as papain, glucoamylase; opacifying agents, pigments, coloring agents and fluoride ion providing salts having anticaries efficacy such as sodium fluoride, potassium fluoride, a tin fluoride such as stannous fluoride.

In one embodiment, the tooth whitening composition has the following general formula:

| Component | Content |
| --- | --- |
| Hydrophobic Polymer Carrier | 1 to 80 wt % |
| Adhesive Enhancing Agent | 0 to 20 wt % |
| Whitening Agent (Peroxide) | 0.5 to 50 wt % |

-continued

| Component | Content |
| --- | --- |
| Surfactant | 0 to 50 wt % |
| Flavor | 0.1 to 1 wt % |
| Other Components (can be HOH) | 0 to 10 wt % |

Dental Trays

In various embodiments of the present invention, the teeth whitening system comprises a dental tray operable to conform to the surface of a tooth or plurality of teeth. The tooth whitening composition can be applied to the surface of the dental tray by manual application, such as by painting. Thus, the dental tray is operable to retain whitening composition and to be inserted into the oral cavity. Further, the dental tray preferably has one or more surfaces that are operable to confront at least one surface of a tooth that is to be whitened.

Dental trays are well-known in the art. A dental tray can be generic (e.g., off-the-shelf) or custom designed for the subject (human or other animal) with which it is to be used. In either type of dental tray, a surface of the tray is contacted with the tooth (usually with multiple teeth), and the whitening composition is permitted to bathe or coat the tooth/teeth. The dental tray will fit within a subject's mouth, and may cover all of the upper or lower teeth or a portion thereof. In certain embodiments, one dental tray may fit over both the upper and lower teeth, such as a mouth guard typically worn by athletes. The dental tray comprises a tooth bed or reservoir formed between an inner and an outer sidewall. The teeth are placed into the tooth bed. The outer sidewall will accordingly be disposed between the outer surface of the teeth and a patient's cheeks, and the inner sidewall will be disposed between the inner surface of the patient's teeth and the mouth cavity. Dental trays designed to simultaneously fit over the upper and lower teeth preferably include air passages to permit the wearer of the dental tray to breathe.

The dental tray can be of any conventional form and made from conventionally used thermoplastic polymers. Thermoset polymers also can be used. Consequently, the tray can range from highly flexible to a low flexibility. The thermoplastic polymers useful in various embodiments of the present invention include polyethylene and polypropylene polymers their derivatives and copolymers, silicone elastomers, polyurethanes and derivatives, polycaprolactams, polystyrene and derivatives, polybutadiene and derivatives, polyisoprene and derivatives, and polymethacrylate and its derivatives. These can be in a sheet, foam or a laminate form. In forming a customized dental tray, a cast is taken of the teeth and gum area of a patient and set. A thermoplastic polymer film is placed over the cast and vacuum formed to the shape of the teeth and gum margin of the patient. In this manner, a tray in the shape of the teeth having a reservoir or bed that can contain a whitening formulation is formed, and can thus be used to treat the patient's teeth.

In one embodiment, the whitening composition is applied by the end-user (a consumer or dental care professional) to the surfaces of the dental tray prior to use, such that the whitening composition contacts the surfaces of the teeth to be whitened. In an alternate embodiment, the whitening composition may be applied to the dental tray and shipped to the end-user with the whitening composition contained in a storage reservoir.

Tooth Whitening Kit

In an embodiment according to the present invention, a tooth whitening kit is provided, for whitening the surface of a tooth in the oral cavity of a human or other animal subject, comprising a dental tray operable for insertion into the oral cavity of the subject comprising a reservoir. Such a dental tray may be selected to correspond to any of the embodiments described above or of those known to one of skill in the art. The tooth whitening kit further comprises a tooth whitening composition comprising a peroxide whitening agent and a hydrophobic siloxane polymer carrier having a viscosity of at least about 50,000 centipoise. In one embodiment, the tooth whitening kit may be employed to the surface of a tooth in the oral cavity of a human or other animal subject using the kit described above, where the whitening composition is applied to the reservoir in the dental tray of the kit and the tray is then inserted into the oral cavity so that the whitening composition is contacted with the surface of the tooth.

Methods

In one embodiment, the present invention provides a method of whitening the surface of a tooth in the oral cavity of a human or other animal subject using a tooth whitening system comprising a dental tray having a surface operable to confront a tooth surface, and a tooth whitening composition comprising a whitening agent and a hydrophobic polymer carrier. The method comprises applying the composition to the dental tray and inserting the tray into the oral cavity so that the composition is contacted with the surface of the tooth. The contacting occurs for a duration of time sufficient to satisfactorily effect whitening of the teeth. Thus, the contacting occurs for a sufficient period of time to at least partially whiten teeth. This can be a period of time from about 0.5 hour to 2 hours or longer. The substantially non-aqueous tooth whitening composition is effective over a longer period of time, since it is not significantly diluted or removed from the dental tray during the treatment time.

In another embodiment, a method of whitening a surface of a tooth is provided comprising contacting the surface with a whitening composition contained in a dental tray, where the whitening composition comprises a whitening agent and a hydrophobic polymer carrier. In certain embodiments, before the contacting, a dental tray is formed that substantially conforms to a surface of a tooth, or a plurality of teeth, to be whitened. Further, after the contacting, the method comprises removing the dental tray from the surface of the tooth and then treating the surface of the tooth with a desensitizing composition in certain embodiments. The tooth desensitizing formulation can be applied via use of the dental tray. In alternate embodiments, the desensitizing composition is applied via use of a desensitizing toothpaste for several days after the whitening procedure. Such desensitizing formulations preferably contain at least one of the following: potassium nitrate, citric acid, citric acid salts, strontium chloride and the like. A process where the tooth whitening procedure is followed by a tooth desensitizing procedure is preferred for subjects who are susceptible to tooth sensitivity problems.

The liquid whitening compositions of the present invention are prepared by adding and mixing the ingredients of the composition in a suitable vessel such as a stainless steel tank provided with a mixer. In the preparation of the liquid whitening composition, the ingredients are advantageously added to the mixer in the following order: liquid anhydrous silicone based pressure sensitive polymer (hydrophobic polymer carrier), peroxide whitening agent, adhesion enhancing agent and any desired flavoring or sweetener. The ingredients are then mixed to form a homogeneous dispersion/solution. The moisture content of the tooth whitening composition will be about 0.05% by weight to about 10% by weight, and preferably about 2% by weight to about 8% by weight. The viscosity of such a composition is about 50,000 centipoise to about 900,000 centipoise and preferably about 200,000 centipoise to about 600,000 centipoise.

EXAMPLES

The present invention is illustrated by the following examples but is not to be limited thereby.

Examples 1-4

The formulations in the following Table 1 are formed by adding silicone hydrophobic polymers commercially available as Dow Corning Q7-9120 and Dow Corning 8-7016 in a dimethicone solvent to a Brogli mixer. These two components are mixed for 30 minutes at high speed without vacuum. Sodium saccharin is added and mixed continuously for 3 minutes at high speed without vacuum. A COP Plastigel 5 is then added and mixed continued for 10 minutes at high speed without vacuum. The Polyplasdoxyl XL10, 35% hydrogen peroxide peralkali and flavor are added and mixed on low speed without vacuum for 5 minutes. Full vacuum is then applied and the formulation is mixed at high speed for an additional 15 minutes.

TABLE 1

| Ingredient | Example 1 (Wt. %) | Example 2 (Wt. %) | Example 3 (Wt. %) | Example 4 (Wt. %) |
|---|---|---|---|---|
| Dow Corning 8-7016 | 30.0 | 30.0 | 30.0 | 30.0 |
| Dow Corning Q7-9120 | 20.0 | 16.46 | — | 20.0 |
| Pluracare L 1220 | — | — | — | 0.05 |
| Polyplasdone XL-10 | 25.0 | 25.0 | 25.0 | 25.0 |
| COP Plastigel 5 (Lyne Labs) | 20.1 | 15.5 | — | 11.91 |
| 35% Hydrogen Peroxide Peralkali | 4.0 | 12.14 | 44.1 | 12.14 |
| Sodium Saccharin | 0.3 | 0.3 | 0.30 | 0.30 |
| VW Mint Flavor | 0.6 | 0.6 | 0.6 | 0.60 |
| Viscosity centipoises (cP) | 180,000 | 180,000 | 270,000 | 360,000 |

The formulations of Examples 1-4 have viscosities of about 180,000 cP to 360,000 cP. These formulations will have a workable consistency when being applied to a tray and in adherence to teeth. There also is a low loss of the composition from the tray by the natural flushing action of saliva.

What is claimed is:

1. A tooth whitening composition having an overall viscosity of greater than 50,000 centipoise and less than 900,000 centipoise, comprising:
   between 0.5 to about 50 weight % of a whitening agent selected from the group consisting of peroxides, chlorites and hypochlorites;
   between 1 to about 80 weight % of pressure-sensitive, hydrophobic polymer carrier comprising silicone resin and polydiorganosiloxane;
   between 0.1 to 1 weight % of a flavoring agent; and
   between 2 to 15 weight % of an adhesion enhancing agent consisting of polyethylene gelled mineral oil that augments adhesion of said tooth whitening composition to tooth surfaces.

2. The tooth whitening composition according to claim 1, wherein said whitening composition has a viscosity of between about 200,000 centipoise to about 600,000 centipoise.

3. The tooth whitening composition according to claim 1, wherein the tooth whitening composition is contained in a dental tray.

4. The tooth whitening composition according to claim 3, wherein said dental tray is a material selected from the group consisting of: a thermoplastic resin and a thermoset resin.

5. A tooth whitening composition having an overall viscosity of greater than 50,000 centipoise and less than 900,000 centipoise, comprising:
   between about 0.1 to about 1 weight % of a whitening agent selected from the group consisting of peroxides, chlorites and hypochlorites;
   between 1 to about 80 weight % of a pressure-sensitive, hydrophobic polymer carrier comprising silicone resin and polydiorganosiloxane;
   between 0.1 to 1 weight % of a flavoring agent; and
   between 2 to 15 weight % of an adhesion enhancing agent consisting of polyethylene gelled mineral oil that augments adhesion of said tooth whitening composition to tooth surfaces.

6. The tooth whitening composition according to claim 5, wherein said whitening composition has a viscosity of between about 200,000 centipoise to about 600.00 centipoise.

7. The tooth whitening composition according to claim 5, wherein the tooth whitening composition is contained in a dental tray.

8. The tooth whitening composition according to claim 7, wherein said dental tray is a material selected from the group consisting of: a thermoplastic resin and a thermoset resin.

* * * * *